(12) United States Patent
Opolski et al.

(10) Patent No.: US 7,419,498 B2
(45) Date of Patent: Sep. 2, 2008

(54) QUICK RELEASE KNOT ATTACHMENT SYSTEM

(75) Inventors: Steven Opolski, Carlisle, MA (US); Sean Forde, Watertown, MA (US)

(73) Assignee: NMT Medical, Inc., Boston, MA (US)

( * ) Notice: Subject to any disclaimer, the term of this patent is extended or adjusted under 35 U.S.C. 154(b) by 426 days.

(21) Appl. No.: 10/944,512

(22) Filed: Sep. 17, 2004

(65) Prior Publication Data
US 2005/0085843 A1    Apr. 21, 2005

Related U.S. Application Data

(60) Provisional application No. 60/513,089, filed on Oct. 21, 2003.

(51) Int. Cl.
*A61B 17/08* (2006.01)
*A61D 1/00* (2006.01)
*A61F 2/02* (2006.01)

(52) U.S. Cl. ..................... 606/215; 623/23.72
(58) Field of Classification Search .......... 606/200, 606/213, 215
See application file for complete search history.

(56) References Cited

U.S. PATENT DOCUMENTS

| | | | |
|---|---|---|---|
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,425,908 A | 1/1984 | Simon |
| 4,696,300 A | 9/1987 | Anderson |
| 4,836,204 A | 6/1989 | Landymore et al. |
| 4,915,107 A | 4/1990 | Rebuffat et al. |
| 4,917,089 A | 4/1990 | Sideris |
| 5,021,059 A | 6/1991 | Kensey et al. |
| 5,037,433 A | 8/1991 | Wilk et al. |
| 5,041,129 A | 8/1991 | Hayhurst et al. |
| 5,108,420 A | 4/1992 | Marks |

(Continued)

FOREIGN PATENT DOCUMENTS

EP    1013227    12/1999

(Continued)

OTHER PUBLICATIONS

National Aeronautics and Space Administration, "55-Nitinol—The Alloy With a Memory: Its Physical Metallurgy, Properties, and Applications," NASA-SP 5110, pp. 24-25.

(Continued)

*Primary Examiner*—Kevin T. Truong
*Assistant Examiner*—Christina D Gettman
(74) *Attorney, Agent, or Firm*—Kirkpatrick & Lockhart Preston Gates Ellis LLP

(57) ABSTRACT

A medical delivery system for delivering or retrieving a medical implant. In one embodiment, the medical delivery system includes a tube having a lumen; an implant; and a suture releasably joined to the implant, the suture comprising a first end, a second end, and a releasable knot, wherein tension applied to the first end of the suture collapses at least a portion of the implant for introduction into the tubular lumen and tension applied to the second end of the suture releases the implant.

25 Claims, 13 Drawing Sheets

U.S. PATENT DOCUMENTS

| | | | |
|---|---|---|---|
| 5,192,301 A | 3/1993 | Kamiya et al. |
| 5,222,974 A | 6/1993 | Kensey et al. |
| 5,236,440 A | 8/1993 | Hlavacek |
| 5,257,637 A | 11/1993 | El Gazayerli |
| 5,282,827 A | 2/1994 | Kensey et al. |
| 5,284,488 A | 2/1994 | Sideris |
| 5,304,184 A | 4/1994 | Hathaway et al. |
| 5,312,435 A | 5/1994 | Nash et al. |
| 5,334,217 A | 8/1994 | Das |
| 5,354,308 A | 10/1994 | Simon et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,507,811 A | 4/1996 | Koike et al. |
| 5,540,712 A | 7/1996 | Kleshinski et al. |
| 5,577,299 A | 11/1996 | Thompson et al. |
| 5,601,571 A | 2/1997 | Moss |
| 5,618,311 A | 4/1997 | Gryskiewicz |
| 5,634,936 A | 6/1997 | Linden et al. |
| 5,683,411 A | 11/1997 | Kavteladze et al. |
| 5,702,421 A | 12/1997 | Schneidt |
| 5,709,707 A | 1/1998 | Lock et al. |
| 5,720,754 A | 2/1998 | Middleman et al. |
| 5,725,552 A | 3/1998 | Kotula et al. |
| 5,733,294 A | 3/1998 | Forber et al. |
| 5,741,297 A | 4/1998 | Simon |
| 5,776,162 A | 7/1998 | Kleshinski |
| 5,797,960 A | 8/1998 | Stevens et al. |
| 5,810,884 A | 9/1998 | Kim |
| 5,823,956 A | 10/1998 | Roth et al. |
| 5,829,447 A | 11/1998 | Stevens et al. |
| 5,855,614 A | 1/1999 | Stevens et al. |
| 5,861,003 A | 1/1999 | Latson et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,944,738 A | 8/1999 | Ampaltz et al. |
| 5,976,174 A | 11/1999 | Ruiz |
| 5,989,268 A | 11/1999 | Pugsley, Jr. et al. |
| 5,993,475 A | 11/1999 | Lin et al. |
| 6,010,517 A | 1/2000 | Baccaro |
| 6,024,756 A | 2/2000 | Huebsch et al. |
| 6,030,007 A | 2/2000 | Bassily et al. |
| 6,056,760 A | 5/2000 | Koike et al. |
| 6,077,291 A | 6/2000 | Das |
| 6,079,414 A | 6/2000 | Roth |
| 6,080,182 A | 6/2000 | Shaw et al. |
| 6,113,609 A | 9/2000 | Adams |
| 6,117,159 A | 9/2000 | Huebsch et al. |
| 6,132,438 A | 10/2000 | Fleischman et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,228,097 B1 | 5/2001 | Levinson et al. |
| 6,245,080 B1 | 6/2001 | Levinson |
| 6,270,515 B1 | 8/2001 | Linden et al. |
| 6,277,125 B1 * | 8/2001 | Barry et al. ............... 606/108 |
| 6,277,138 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,312,446 B1 | 11/2001 | Huebsch et al. |
| 6,315,791 B1 | 11/2001 | Gingras et al. |
| 6,319,263 B1 | 11/2001 | Levinson |
| 6,342,064 B1 | 1/2002 | Koike et al. |
| 6,344,049 B1 | 2/2002 | Levinson et al. |
| 6,348,041 B1 | 2/2002 | Klint |
| 6,352,552 B1 | 3/2002 | Levinson et al. |
| 6,355,052 B1 | 3/2002 | Neuss et al. |
| 6,364,853 B1 | 4/2002 | French et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,416,536 B1 * | 7/2002 | Yee ............... 623/1.11 |
| 6,440,152 B1 | 8/2002 | Gainor et al. |
| 6,460,749 B1 | 10/2002 | Levinson et al. |
| 6,488,706 B1 | 12/2002 | Solymar |
| 6,494,888 B1 | 12/2002 | Laufer et al. |
| 6,551,344 B2 * | 4/2003 | Thill ............... 606/213 |
| 2001/0034537 A1 | 10/2001 | Shaw et al. |
| 2001/0037129 A1 | 11/2001 | Thill |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0029048 A1 | 3/2002 | Miller |
| 2002/0032462 A1 | 3/2002 | Houser et al. |
| 2002/0043307 A1 | 4/2002 | Ishida et al. |
| 2002/0077555 A1 | 6/2002 | Schwartz |
| 2002/0099389 A1 | 7/2002 | Michler et al. |
| 2002/0129819 A1 | 9/2002 | Feldman et al. |
| 2002/0183786 A1 | 12/2002 | Girton |
| 2002/0183787 A1 | 12/2002 | Wahr et al. |
| 2003/0059640 A1 | 3/2003 | Marton et al. |
| 2003/0181945 A1 | 9/2003 | Opolski |
| 2003/0187495 A1 * | 10/2003 | Cully et al. ............... 623/1.15 |
| 2003/0195530 A1 | 10/2003 | Thill |
| 2004/0176797 A1 | 9/2004 | Opolski |

FOREIGN PATENT DOCUMENTS

| | | |
|---|---|---|
| WO | WO00/27292 | 5/2000 |
| WO | WO01/08600 | 2/2001 |
| WO | WO01/49185 | 7/2001 |
| WO | WO01/93783 | 12/2001 |

OTHER PUBLICATIONS

Kimura, et al., "Effects of Neutron Irradiation on the Transformation Behavior in Ti-Ni Alloys," Proceedings of the International Conference on Martensitic Transformations, 1992, pp. 935-940.

Ramanathan, et al., "Experimental and Computational Methods for Shape Memory Alloys," 15th ASCE Engineering Mechanics Conference, Jun. 2-5, 2002.

Shabalovskaya, "Surface, Corrosion and Biocompatibility Aspects of Nitinol as an Implant Material," Bio-Medical Materials and Engineering 12, 2002, pp. 69-109.

Uchil, "Shape Memory Alloys—Characterization Techniques," PRAMANA—Journal of Physics, vol. 58, Nos. 5 & 6, May & Jun. 2002, pp. 1131-1139.

* cited by examiner

QUICK RELEASE KNOT ATTACHMENT SYSTEM

RELATED APPLICATIONS

This application claims priority to and the benefit of U.S. Provisional Patent Application No. 60/513,089, filed Oct. 21, 2003, the disclosure of which is incorporated herein by reference.

TECHNICAL FIELD

The invention relates generally to coupling and release devices used in a delivery and retrieval system and their uses in connection with delivering or retrieving a medical implant.

BACKGROUND OF THE INVENTION

Numerous systems for catheter delivery of implants have been devised over the years in order to assist medical operators in delivering and positioning implants, for example, occluders, within a patient, preferably in a minimally invasive manner. A problem with many of the known delivery systems is their limited flexibility for positioning or retrieving the implant.

Most implant delivery systems include an elongated catheter that is used to access various passageways inside a patient's body. Often the desired position of the implant may not align with the longitudinal axis of the catheter. Upon release of the implant, the implant may shift position causing possible trauma to the surrounding tissue as the distal end of the catheter springs back to a more relaxed state. Such shifting in the implant position may result in a less desirable medical result (such as device embolization or a residual leak in the case of septal occluders).

Implants may include devices designed for compression into a small size tube or catheter to facilitate their introduction into the vasculature of the patient. The implants are subsequently expandable either to occlude defects or holes in the heart, in the case of intracardiac septal occluders, or to contact the walls of the passageway (e.g., blood vessels), in the case of vena cava filters or stents. Among these devices are septal occluders well-known in the art such as the occluder described in U.S. Pat. No. 5,425,744 issued to Fagan et al. Septal occluders are useful in treating medical conditions such as patent foramen ovale (PFO), which is a persistent, one-way, often flap-like opening in the wall between the right atrium and left atrium of the heart, as well as other congenital and acquired defects in the heart or vasculature.

Various types of attachment mechanisms for delivering and releasing an intracardiac occluder are known in the art such as threaded male and female members as described in U.S. Pat. No. 5,725,552 issued to Kotula et al. or ball-to-ball (or pin-to-pin) attach/release mechanisms, such as the attach/release mechanism illustrated in *Transcatheter Therapy in Pediatric Cardiology* (1993): 335-348. These systems, however, provide little versatility with respect to positioning the implant and disconnecting the implant from the delivery device.

Accordingly, there is a need to provide a delivery system that is capable of reversibly receiving an implant so as to easily retrieve the implant should it be positioned incorrectly and which also has a flexible attachment system for release of the implant once it is positioned.

SUMMARY OF THE INVENTION

The present invention provides coupling systems and related methods, which are useful for delivering, positioning, repositioning, reversibly retrieving and releasing an implant, such as a septal occluder, into and out of a patient.

In one aspect, the invention features a device for delivering a medical implant including a tube such as a catheter or sheath having a lumen or a wire and a suture releasably joined to the implant. The suture comprises a first end, a second end, and a releasable knot, wherein applying tension to the first end of the suture collapses at least a portion of the implant for introduction into the tubular lumen and applying tension to the second end of the suture releases the suture from the implant.

In one embodiment, the suture is attached to a proximal portion of the implant. In another embodiment, the suture is attached to a coil. In another embodiment, the first end and the second end of the suture are operatively joined to an actuator. In one embodiment, the suture is joined to the implant at a plurality of attachment sites.

In one embodiment, the knot is a quick release knot or a slip knot. In another embodiment, the knot is a Highwayman's hitch knot. Preferably the knot is so configured that tension applied to the first end of the suture tightens the knot and tension applied to the second end of the suture releases the knot. In one embodiment, tension on the first end of the suture collapses at least a portion of the implant, e.g., the proximal portion of the implant, for reintroduction into the tubular lumen. The implant of the invention may occlude any portion of a vessel or an organ. For example, the implant may be a septal occluder.

In one embodiment, the medical delivery device further contains a grasper. In one embodiment, the grasper has a fixed jaw position. In another embodiment, the grasper has a pivotal jaw. In one embodiment, the device further contains an elongated member wherein the grasper is joined to the elongated member. In another embodiment, the elongated member is operatively joined to an actuator.

In another aspect, the invention features a medical delivery system for delivering an implant to an anatomical site in a patient's body. The medical delivery system includes a tube comprising a lumen for slideably receiving the implant and a suture slideably receivable in said lumen comprising a first end, a second end, and a knot, wherein the suture is releasably joined to the implant by the knot, the implant being released from the suture when tension is applied to an end of the suture. In one embodiment, the suture is attached to the proximal portion of the implant via a suture attachment point such as a coil. The implant of the invention may occlude any portion of a vessel or an organ. For example, the implant may be a septal occluder.

In one embodiment, the knot is a quick release knot or a slip knot. Tension applied to the first end of the suture tightens the knot and tension applied to the second end of the suture releases the knot. Tension applied to the first end of the suture collapses at least a portion of the implant for introduction into the lumen of the tube. In one embodiment, the tube is operatively joined to an actuator.

In another aspect, the invention features an attachment system for a medical implant. The attachment system includes a suture having a first end, a second end, and a knot, wherein the suture is releasably joined to an implant by the knot, the implant being secured to the suture when tension is applied to the first end of the suture and the implant being released from the suture when tension is applied to the second end of the suture.

In another aspect, the invention features a method of occluding a site in a body of a patient. The method includes providing a medical delivery system for a medical implant which includes a tube comprising a lumen for slideably receiving the implant, an implant, and a suture releasably joined to the implant comprising a first end, a second end, and a releasable knot, wherein applying tension to the first end of the suture collapses at least a portion of the implant for introduction into the tube lumen and applying tension to the second end of the suture releases the knot, and delivering the implant to the site in the body requiring the occlusion. The site in the patient's body may be a vessel. For example, the site may be a patent foramen ovale.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

DETAILED DESCRIPTION OF THE PRESENT INVENTION

The medical delivery system described herein may be used to deliver an implant, for example, an intracardiac occluder, such as a septal occluder for repair of a patent foramen ovale in a patient. The system includes a tube, an elongated member that slides in the lumen of the tube, a coupling device at the distal end of the elongated member that couples to the implant, and sutures that attach to the implant. The sutures also include a quick release knot. The quick release knot may be, for example, a slip knot, a highwayman's hitch knot, or a similar knot that is easily and quickly released. The sutures may serve multiple purposes. For example, the sutures may be used as an attachment system. Moreover, applying tension to the sutures may be used to collapse an expanded implant. This allows for the retrieval of the implant into the tubular lumen of the delivery system after it is released from the tube to the implant site. The presence of the quick release knot provides a releasable fastener that releases the implant from the delivery system at the desired site and, optionally, allows the retrieval of the implant.

The term "implant" as used herein includes devices, carriers, and objects that are placed in the body of a patient by invasive or minimally invasive methods, for example, a percutaneous delivery route. Exemplary implants include, but are not limited to, prosthetic occluders, for example, intracardiac septal occluders, stents, such as intravascular or urinary stents, filters, such as intravascular filters, prostheses, valves, pumps, pace-makers, medications and so on. The implant 40 may be permanent, semi-permanent, or temporary. The implant 40 may be biodegradable. The implant 40 may be removable through an interventional procedure. The implant 40 may be a drug delivery device, such as capsules, tablets, or suppositories, for example, that deliver pharmaceutical agents to the patient. In particular, the term implant includes intracardiac prosthetic occluders, for example, a septal occluder for the closing of, for example, a patent foramen ovale, or an atrial appendage occlusion device or prosthesis, for example, a left atrial appendage occluder device.

Figure 1:
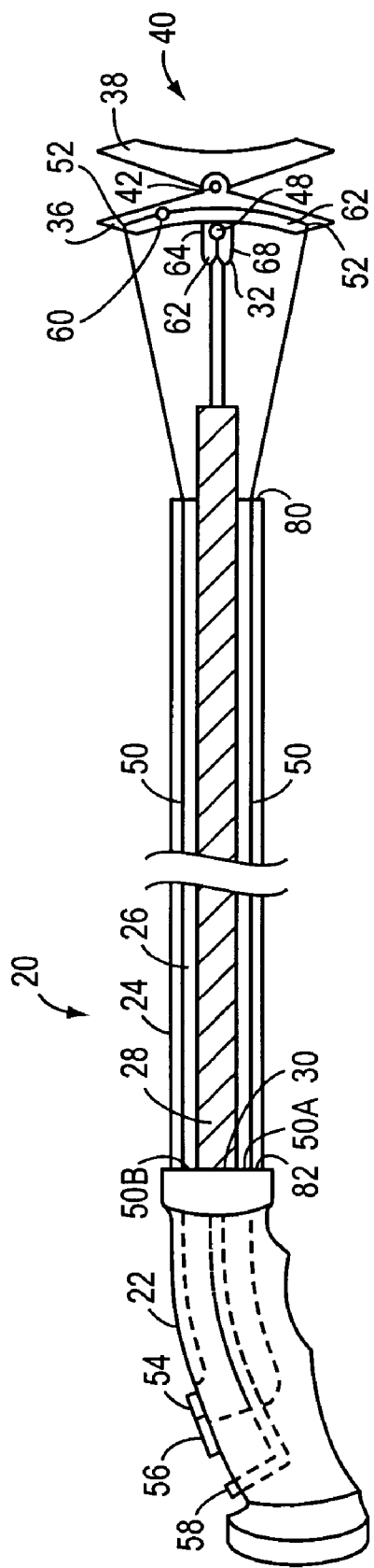
FIG. 1 depicts a delivery device and a deployed implant according to an illustrative embodiment of the invention.
Figure 2:
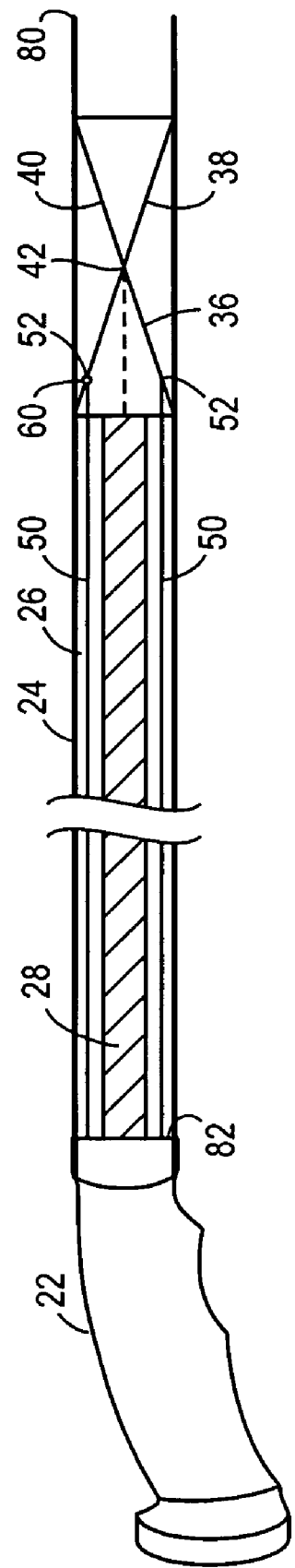
FIG. 2 depicts a delivery device and a collapsed implant according to an illustrative embodiment of the invention.

FIGS. 1 and 2 depict an illustrative embodiment of a medical delivery device 20 which includes a handle 22, a tube 24 such as a catheter or a sheath with an axially disposed lumen 26, and an elongated member 28 that is axially disposed and slideable within the lumen 26 of the tube 24. The tube 24 includes a proximal end 82 and a distal end 80. The elongated member 28 includes a proximal end 30 and a distal end 32.

As depicted in FIG. 1, the exemplary elongated member 28 operatively joins to an actuator 58 positioned on the handle 22 and slideably moves within the lumen 26 of the tube 24. Alternatively, in another embodiment, the elongated member 28 fixes to the handle 22 and the tube 24 operatively joins to an actuator 59 positioned on the handle 22 and slideably moves over the elongated member 28 (not shown). In either case, the actuator causes relative motion of the tube 24 and the member 28. As the terms are used herein, proximal refers to a point closest to the operator and distal refers to a point furthest away from the operator.

FIG. 1 is a schematic view of the medical delivery device 20 with a septal occluder in an expanded position beyond the distal end of the tube according to an illustrative embodiment of the invention. The distal end 32 of the exemplary elongated member 28 reversibly joins to the implant 40. The implant 40 may be, for example, a septal occluder. According to features of this embodiment, the implant 40 includes a proximal portion 36, a distal portion 38 and a connector 42. FIG. 2 depicts the same delivery device 20 and implant 40 illustrated in FIG. 1 with the implant 40 collapsed within the lumen 26 of the tube 24.

Figure 3:
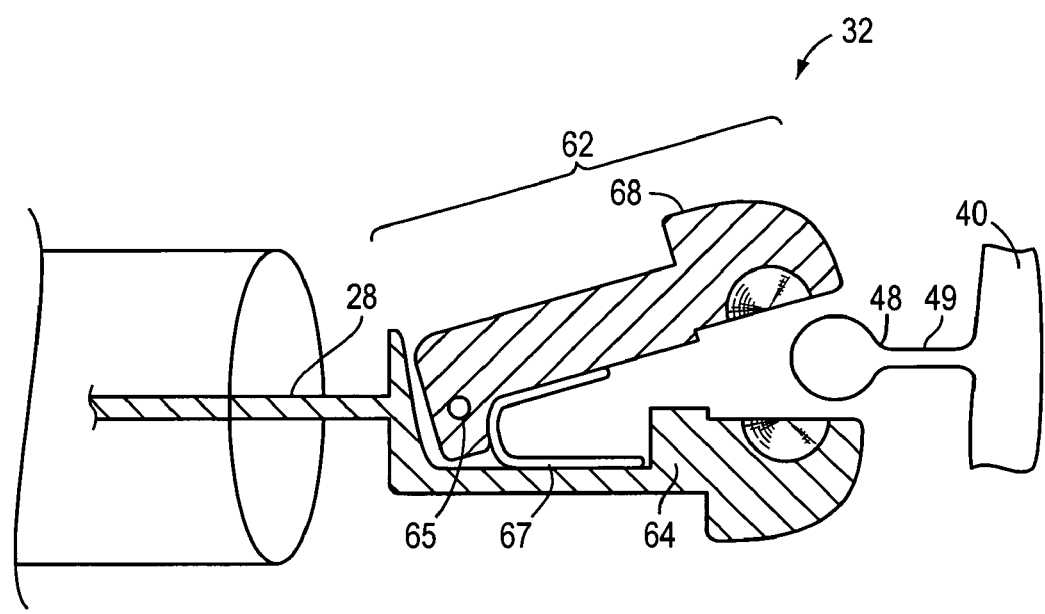
FIG. 3 depicts an enlargement of the distal end of the delivery device shown in FIGS. 1 and 2 including a grasper according to an illustrative embodiment of the invention.

FIG. 3 depicts the distal end 32 of the elongated member 28 according to an illustrative embodiment of the invention. In the illustrative embodiment, the distal end 32 of the elongated member 28 has a grasper 62. In one embodiment of the invention, the grasper 62 is attached to the distal end 32 of the elongate member or, alternatively, in another embodiment, the grasper 62 is an integral part of the elongate member 28. As depicted in the illustrative embodiment shown in FIG. 3, the grasper 62 has jaw 64 and jaw 68 which close and reversibly grip an implant ball 48 positioned at the end of a pin-wire 49 extending from the proximal side of the implant 40. In the illustrative embodiment, the first jaw 64 is fixed, i.e., immovable relative to the second jaw 68, and the second jaw 68 pivots about a pin 65 connecting jaw 64 and jaw 68. The jaws 64 and 68 are biased in the open position by a leaf spring 67. The jaws 64 and 68 are forced closed by the walls of the tube 24 as the member 28 is drawn into the lumen 26 of the tube 28. The position of the jaw 68 is controlled through the actuator 58 on the handle 22 (not shown).

In an alternative embodiment, the first jaw 64 and the second jaw 68 both pivot. An exemplary grasper 62 is disclosed in U.S. application Ser. No. 10/389,471, owned by the common assignee of this application, the disclosure of which is incorporated herein by reference.

Other attachment systems may be used to couple the elongated member 28 of the delivery system 20 to the implant 40. For example, in another embodiment, the distal end 32 of the elongated member 28 is magnetic and the implant 40 includes a bead that is ferromagnetic (not shown). An exemplary magnetic member and bead are disclosed in U.S. application Ser. No. 10/379,058, owned by the common assignee of this application, the disclosure of which is incorporated herein by reference. In yet another embodiment, the distal end 32 of the elongated member 28 includes a socket and the implant 40 includes a ball that reversibly attaches to the socket. An exemplary socket and ball are disclosed in U.S. application Ser. No. 10/389,471, owned by the common assignee of this application, the disclosure of which is incorporated herein by reference.

As depicted, for example, in FIG. 1, according to the illustrative embodiment, the delivery device 20 includes a suture 50 longitudinally and slideably disposable in the lumen 26 of the tube 24. The suture 50 attaches to the implant 40 at a suture attachment point 52 on the implant 40. In the exemplary embodiment, suture ends 50A, 50B are housed in the handle 22. The tensioning of the suture ends 50A, 50B are controlled by, for example, one or more actuators 54, 56 present in the handle 22. Each suture end 50A, 50B is manipulated simultaneously or individually. Alternatively, in another embodiment, the suture ends 50A, 50B pass from the implant 40, along the outside of the tube 24 (not shown) to the operator 24 and are manipulated manually (not shown). The suture 50 may be made from various materials, for example, polyester, silk, nylon, metals or metal alloys such as wire, cable wire, braided wire, and combinations thereof.

Figure 4:
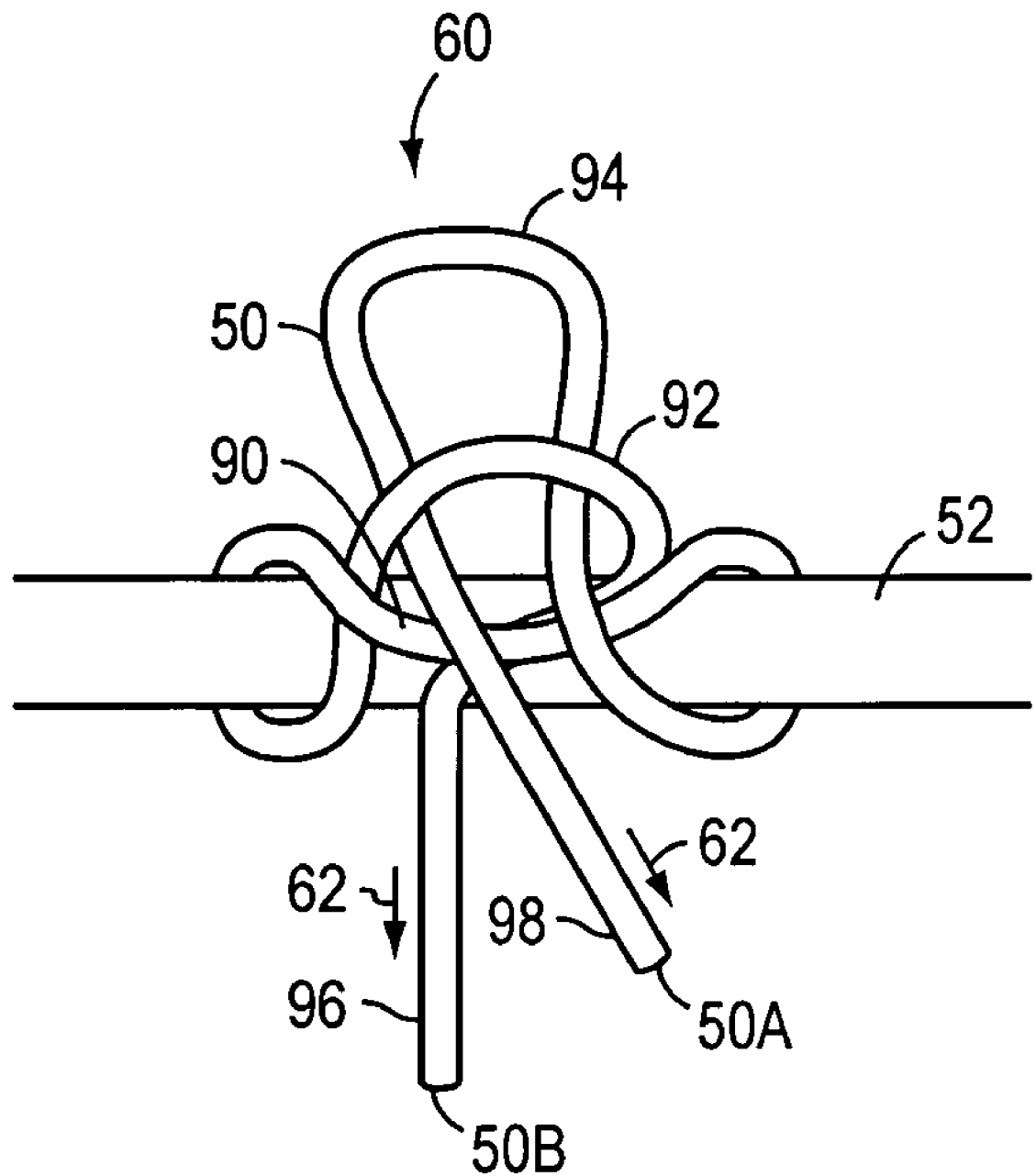
FIG. 4 depicts a highwayman's knot according to an illustrative embodiment of the invention.

FIG. 4 depicts a quick release knot, also known as a slip knot or a highwayman's knot, attached to a suture attachment site 52 on an implant according to an illustrative embodiment of the invention. As depicted, the quick release knot 60 has a first end 50A and a second end 50B extending from the knot 60. When tension is applied to the first end 50B of the suture 50, the knot 60 tightens. The direction of the applied tension is shown by the arrow 62. Alternatively, when tension is applied to the second end 50A of the knot 60, the knot unravels and is released from the attachment site 52. The direction of the applied tension is shown by the arrow 62.

Methods for tying a quick release knot 60 are known in the art. For example, the first step in tying the knot 60 is to make a loop 90 at the suture attachment point 52 with a suture 50. The loop 90 has a first side 96 and a second side 98. A second loop 92 is then made in the first side 96 of suture 50 and is pulled over the suture attachment point 52 and through the first loop 90. A third loop 94 is then made in the second side 98 and is passed through the second loop 92 and over loop 90. The end 50B of the first side 96 is then pulled to dress the knot. The end 50A of the second side 98 may then be pulled abruptly to untie the knot. Other methods for tying the quick release knot, Highwayman's knot, and other slip knots are also contemplated by the invention and are not limited to the knots and methods illustrated.

Figure 5:
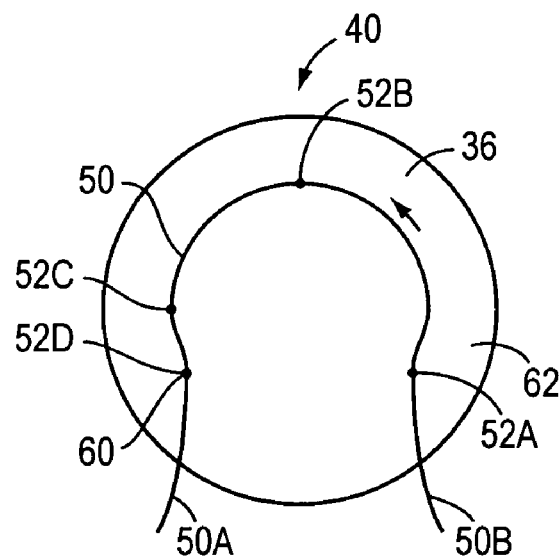
FIG. 5 depicts an implant with an arrangement of suture, suture attachment points and quick release knots according to an illustrative embodiment of the invention.

As depicted, for example, in the plan view of FIG. 5, the suture 50 may be attached to the implant 40 at at least one suture attachment point 52. The suture attachment point 52 may be, for example, a loop on the proximal side 36 of the implant 40 to which the suture 50 attaches. In one embodiment, the suture attachment point 52 is a coil. The number of suture attachment points 52 positioned on the implant 40 may vary. Preferably, the suture 50 may attach to at least two suture attachment points 52 that are positioned on the surface 62 of the proximal portion 36 of the implant 40. The suture attachment points 52 may be configured so that tensioning the suture 50 causes an expanded implant 40 to collapse and the collapsed implant 40 may then be drawn into the tube 24 (not shown) of the delivery system 20. Alternatively, the suture 50 is threaded around the outer surface of the implant 40 by threading the suture 50 through a suture attachment point 52 such as a coil. Typically the suture attachment points 52 may be positioned near the periphery of the implant 40 as illustrated, for example, in FIG. 5. As depicted in FIG. 5, the surface 62 of the proximal portion 36 of an exemplary expanded implant 40 has four suture attachment points 52A, 52B, 52C, 52D. A first end 50A of suture 50 may be threaded through the suture attachment points 52A, 52B, 52C. The first end 50A threads through suture attachment point 52D and a quick release knot 60 is formed at the attachment point 52D. Other patterns of threading the suture through the implant and the location and number of attachment points are also possible and are not limited to the illustrative embodiments.

Figure 6:
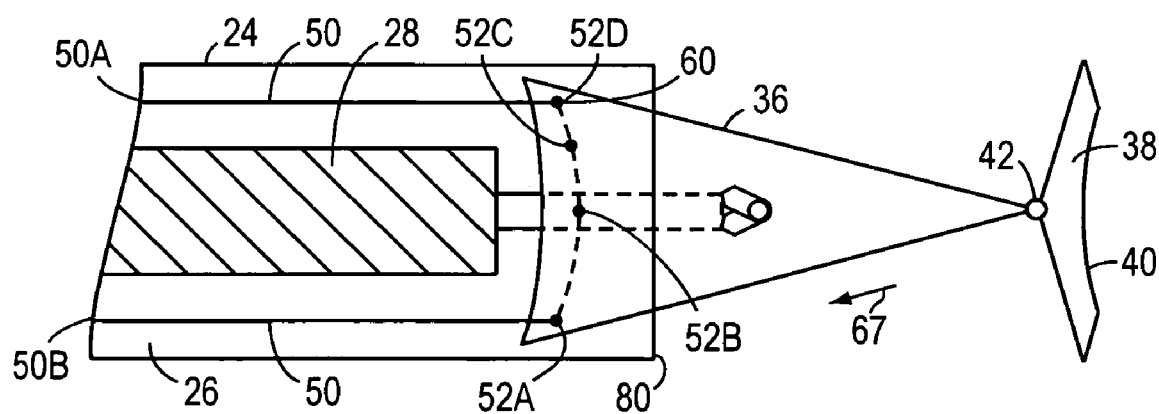
FIG. 6 depicts the distal end of a delivery device and an implant according to an illustrative embodiment of the invention.
Figure 7:
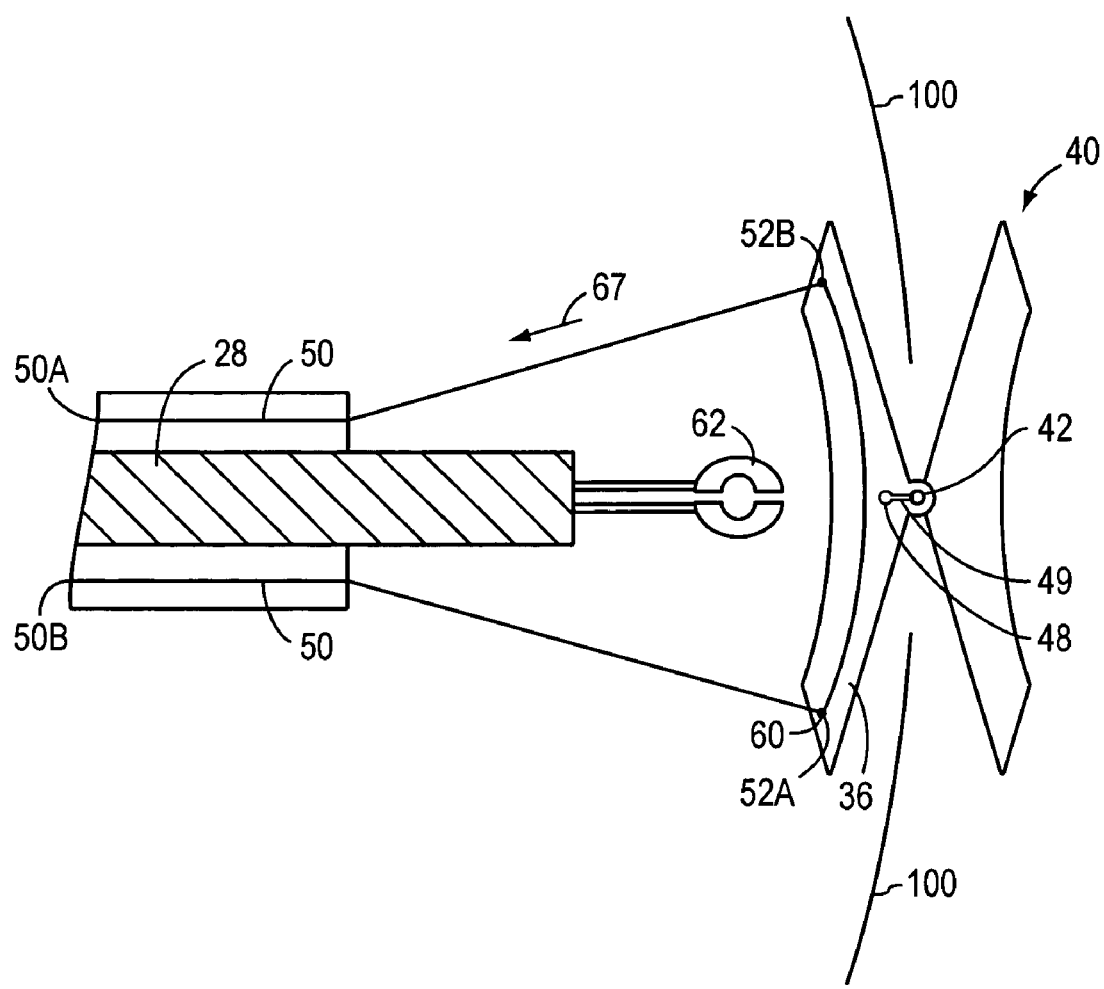
FIG. 7 depicts the distal end of a delivery device and an implant according to an illustrative embodiment of the invention.

FIG. 6 depicts an illustrative step in a method to retrieve an implant after deployment by collapsing the expanded implant 40 into the distal end 80 of the tube 24. As depicted in FIG. 6, suture 50 passes through the suture attachment points 52A, 52B, 52C positioned on the proximal end 36 of the implant 40. The suture 50 is passed to suture point 52D where a quick release knot 60 is formed between the first end 50A and second end 50B of suture 50. Suture 50 threads through the lumen 26 of the delivery tube 24 to the handle 22 where one or more actuators present in the handle 22 are operatively joined to the suture ends 50A, 50B to control the tensioning of the suture ends 50A and 50B (not shown).

As depicted in FIG. 6, when tension is applied in the proximal direction as indicated by arrow 67, and tension in the opposite direction is applied to the elongate member 28, the proximal portion 36 of the implant 40 collapses. The extent to which the implant 40 collapses depends on the amount of tension being applied to the suture end 50B in one direction and the elongated member 28 in the other direction. The diameter of the proximal portion 36 of the expanded implant 40 becomes smaller as tension is applied. As shown, when the outer diameter of the collapsed implant 40 is less than the inner diameter of the lumen 26 of tube 24, the collapsed implant 40 may be drawn into the lumen 26 of the tube 24.

As depicted in FIG. 1, the exemplary elongated member 28 operatively joins to an actuator 58 positioned on the handle 22 and slideably moves within the lumen 26 of the tube 24. Alternatively, in another embodiment, the elongated member 28 fixes to the handle 22 and the tube 24 operatively joins to an actuator 58 positioned on the handle 22 and slideably moves over the elongated member 28 (not shown). In either case, the actuator causes relative motion of the tube 24 and the member 28. As the terms are used herein, proximal refers to a point closest to the operator and distal refers to a point furthest away from the operator.

Figure 8A:
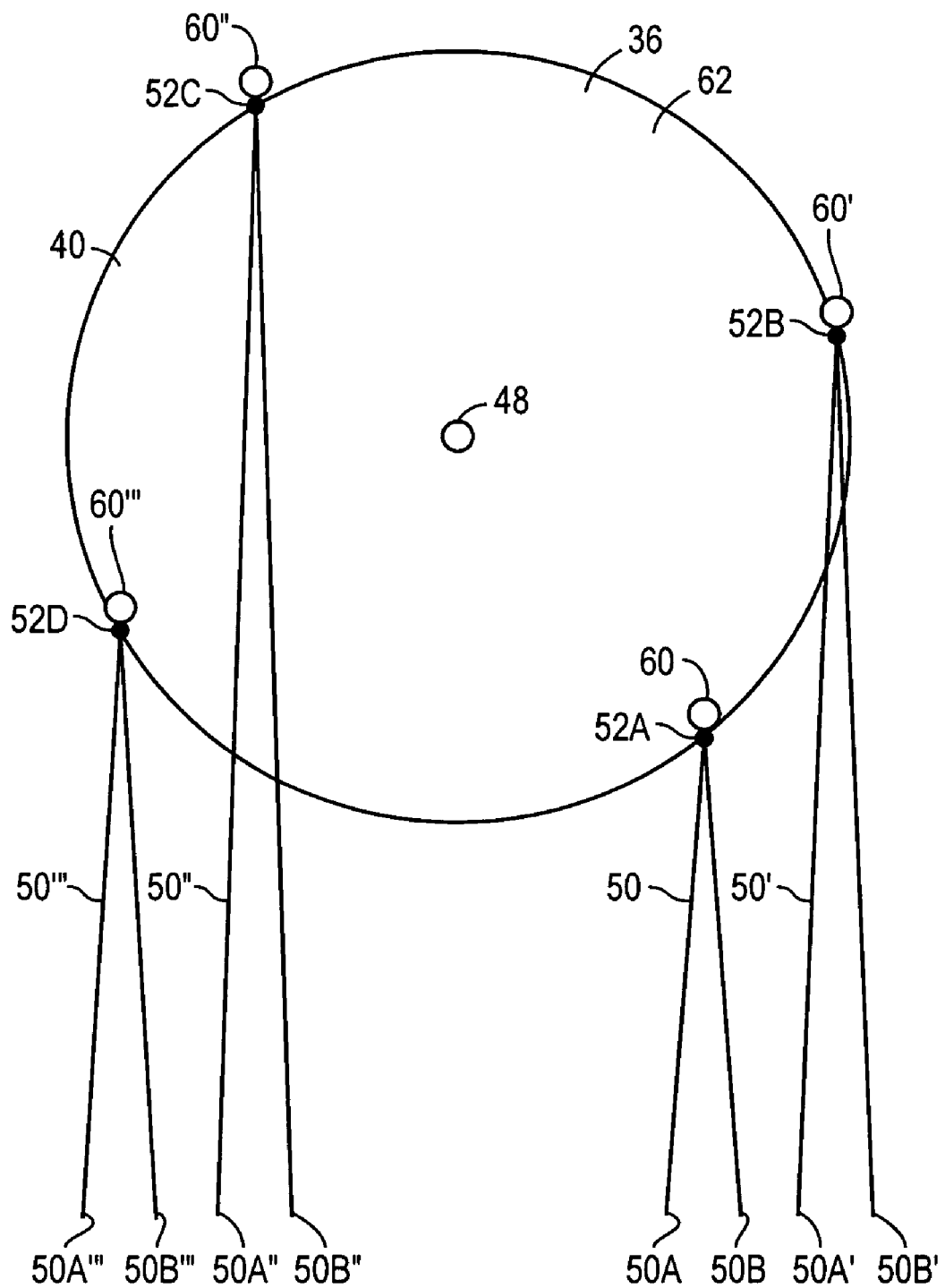
FIG. 8A depicts an arrangement of a suture, suture attachment points and a quick release knot on an implant according to another illustrative embodiment of the invention.
Figure 8B:
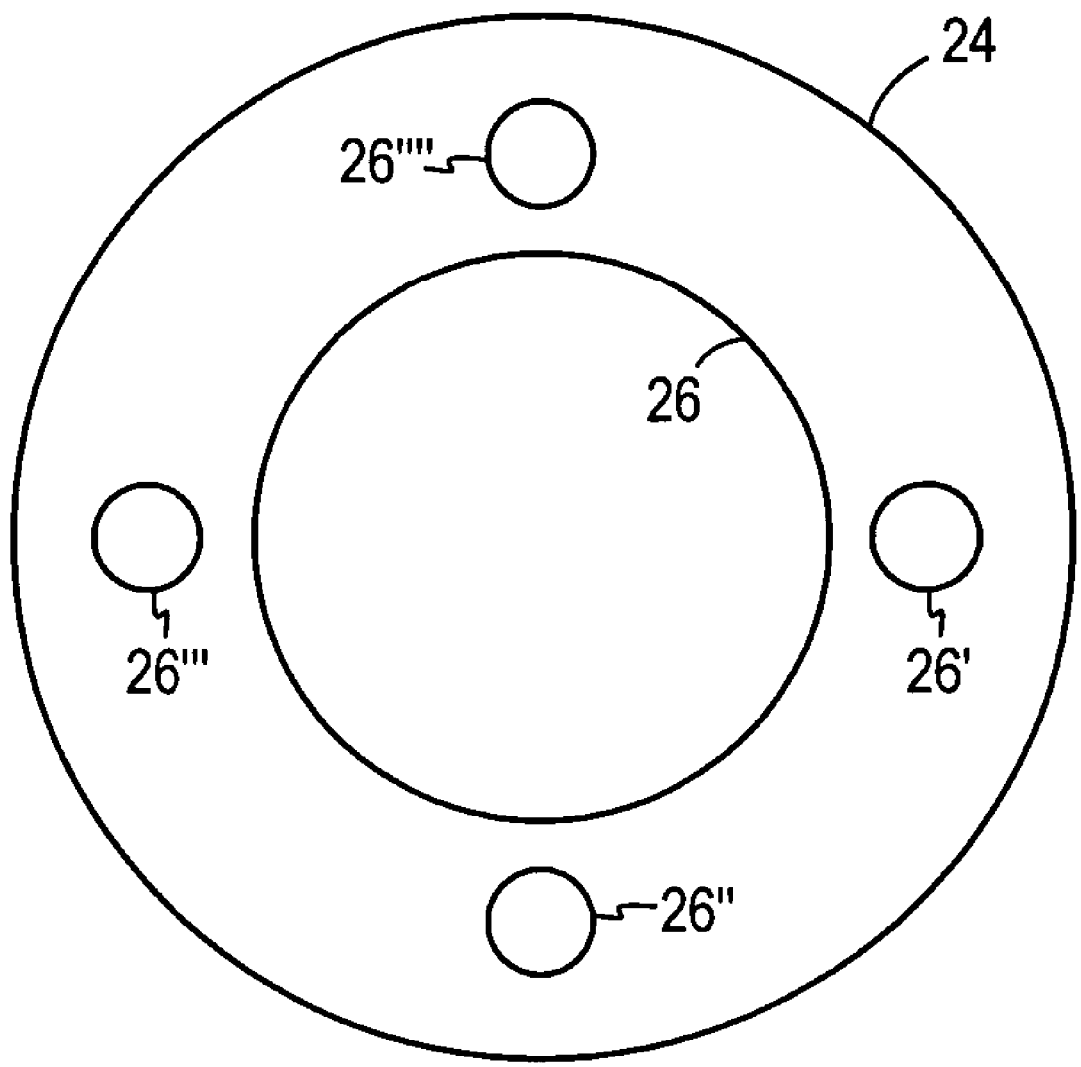
FIG. 8B depicts a traverse section of the delivery device and the arrangement of the delivery device lumen and the suture lumens in another illustrative embodiment of the invention.
Figure 9:
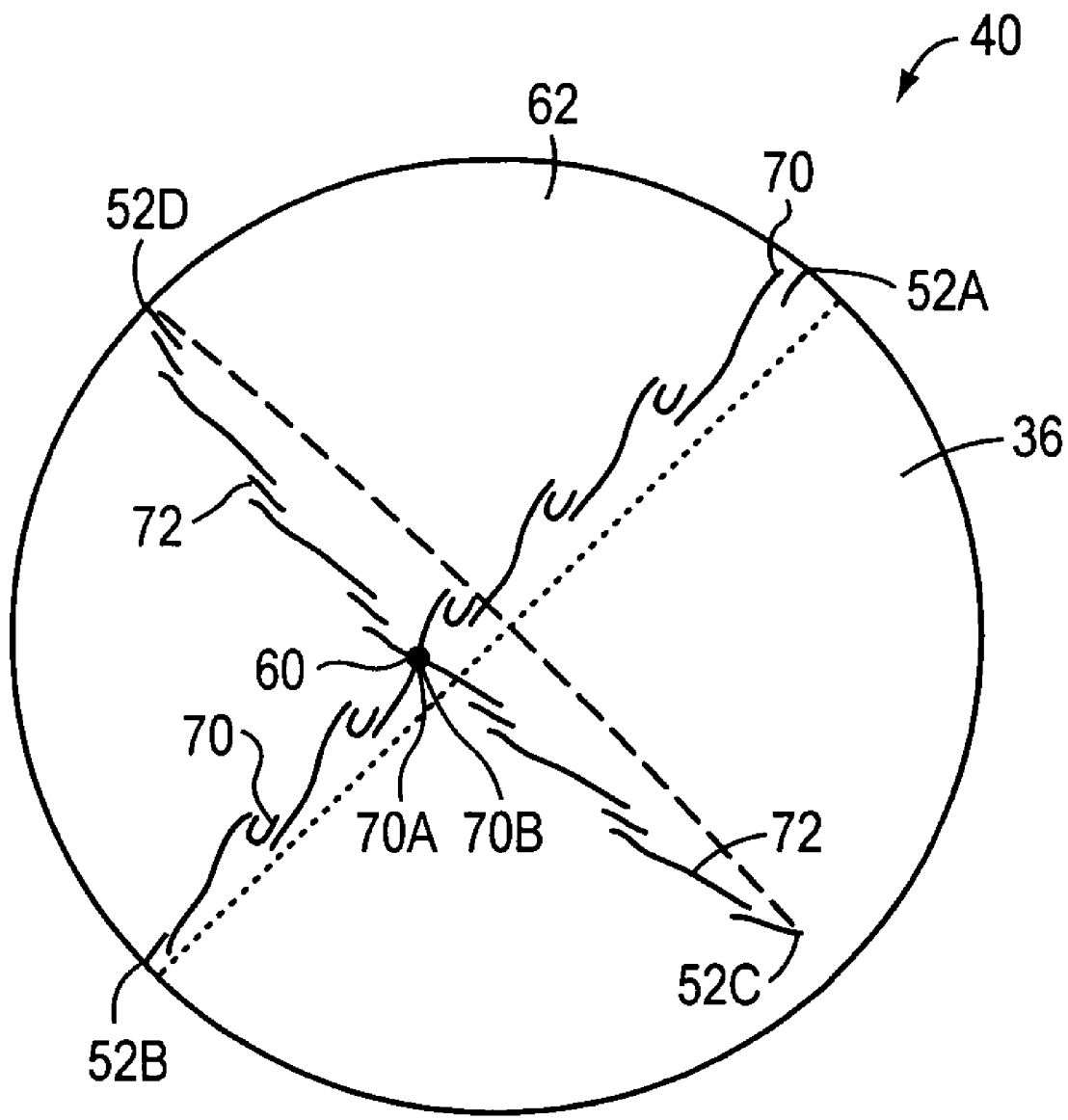
FIG. 9 depicts an arrangement of a suture, suture attachment points and a quick release knot on an implant according to another illustrative embodiment of the invention.

FIG. 8A depicts an arrangement of a suture, suture attachment points, and a quick release knot on an implant according to another illustrative embodiment of the invention. In the illustrative embodiment, a first suture 50, a second suture 50', a third suture 50" and a fourth suture 50''' are attached at four separate suture attachment points 52A, 52B, 52C, 52D, respectively, using a quick release knot 60, 60', 60", 60''' at each attachment point. According to this embodiment, the ends of the first suture 50, the second suture 50', the third suture 50" and the fourth suture 50''', are longitudinally and slideably disposed within the lumen 26 of the delivery tube 24 to the handle 22 (not shown). FIG. 8B depicts a traverse section of the delivery device and the arrangement of the delivery device lumen and the suture lumens in another illustrative embodiment of the invention. According to an alternative embodiment of the invention as depicted in FIG. 8B, the delivery tube 24 may have a lumen 26 for the delivery system 28 (not shown) and up to 20 additional separate lumens, a lumen for each suture 50, for example for separate lumens 26', 26", 26''', and 26'''', for each of the sutures 50, 50', 50", and 50''' (not shown). Applying tension to the suture ends 50A, 50A', 50A" and 50A''' causes the respective quick release knots 60, 60', 60", 60''' to unravel. Applying tension to the suture ends 50B, 50B', 50B" and 50B''' causes the knots 60, 60', 60", 60''' to tighten.

FIG. 3 depicts the distal end 32 of the elongated member 28 according to an illustrative embodiment of the invention. In the illustrative embodiment, the distal end 32 of the elongated member 28 has a grasper 62. In one embodiment of the invention, the grasper 62 is attached to the distal end 32 of the elongate member or, alternatively, in another embodiment, the grasper 62 is an integral part of the elongate member 28. As depicted in the illustrative embodiment shown in FIG. 3, the grasper 62 has jaw 64 and jaw 68 which close and reversibly grip an implant ball 48 positioned at the end of a pin-wire 49 extending from the proximal side of the implant 40. In the illustrative embodiment, the first jaw 64 is fixed, i.e., immovable relative to the second jaw 68, and the second jaw 68 pivots about a pin 65 connecting jaw 64 and jaw 68. The jaws 64 and 68 are biased in the open position by a leaf spring 67. The jaws 64 and 68 are forced closed by the walls of the tube 24 as the member 28 is drawn into the lumen 26 of the tube 24. The position of the jaw 68 is controlled through the actuator 58 on the handle 22 (not shown).

Figure 10A:
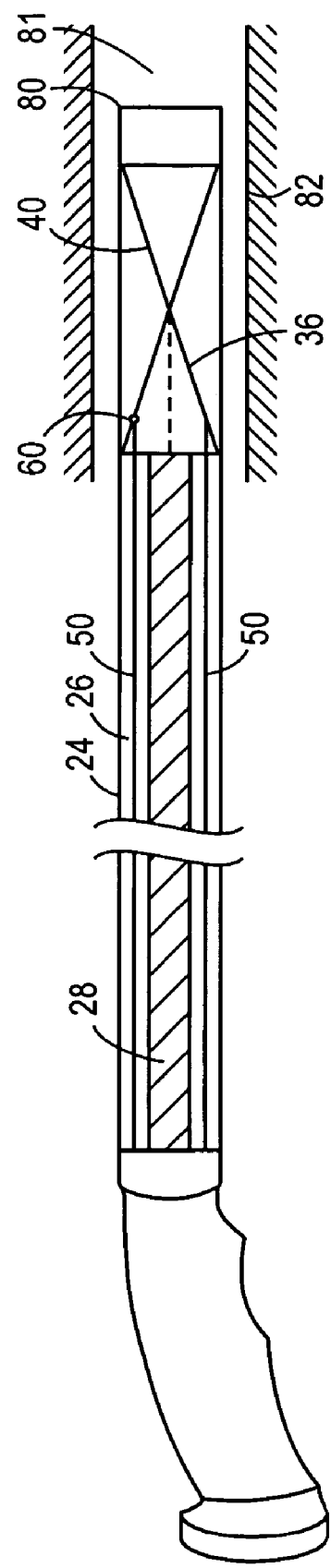
FIGS. 10A-10D depict a method, including a delivery device according to an illustrative embodiment of the invention, for delivering and retrieving an implant in the body of a patient.

FIGS. 10A-10D depict a method for delivering and retrieving an implant 40, such as a septal occluder, to an anatomical site in the body of a patient using a delivery device 20 according to an illustrative embodiment of the invention. FIG. 10A depicts the exemplary delivery device 20. An implant 40 is collapsed in the lumen 26 of the tube 24 and an elongated member 28 that is axially disposed in the lumen 26 of the tube 24. The implant 40 may be attached to the distal end of elongate member 28 of delivery device 20 by a suture 50, which also includes a quick release knot 60. As depicted, the delivery device 20 is introduced by an operator into, for example, the lumen 81 of a vessel 82 in the patient's body.

Figure 10B:
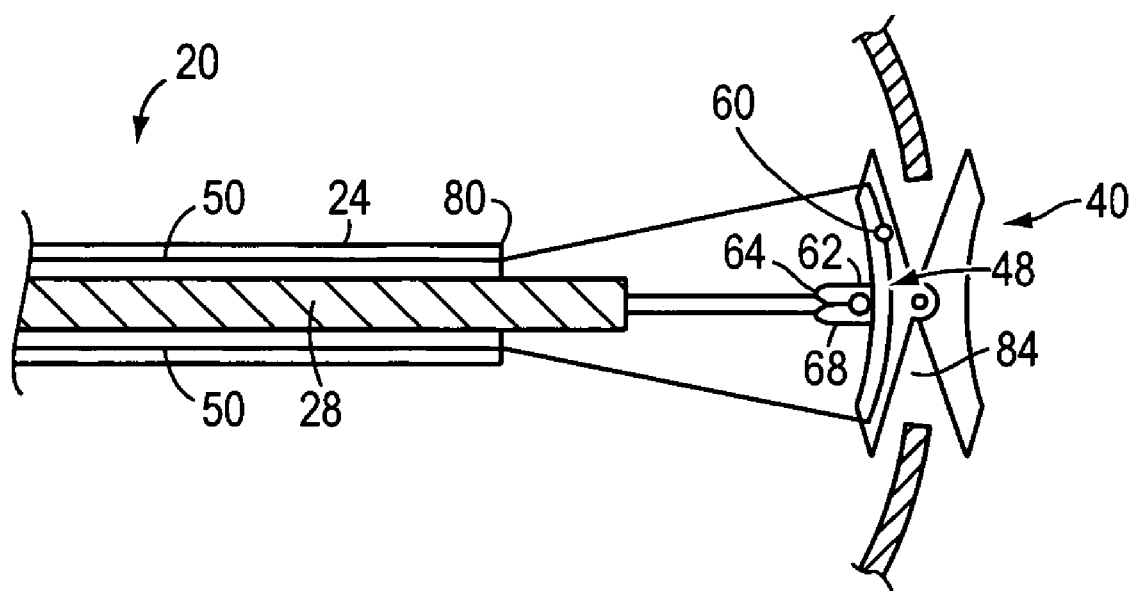

Referring to FIG. 10B, the distal end 80 of the delivery system 20 is threaded through the vessel until the left atrial chamber (not shown) is reached. The implant 40 is positioned at the chosen anatomical site, for example, a patent foramen ovale 84. The operator releases the collapsed implant 40 by, e.g., actuating an actuator button 58 on the handle 22 (not shown) to advance the elongated member 28 and the collapsed implant 40 out of distal end 80 of the tube 24 of the delivery device 20. When the implant 40 is extended beyond the distal end 80 of the tube 24, the implant 40 is deployed and adopts an expanded configuration as shown in FIG. 10B.

Figure 10C:
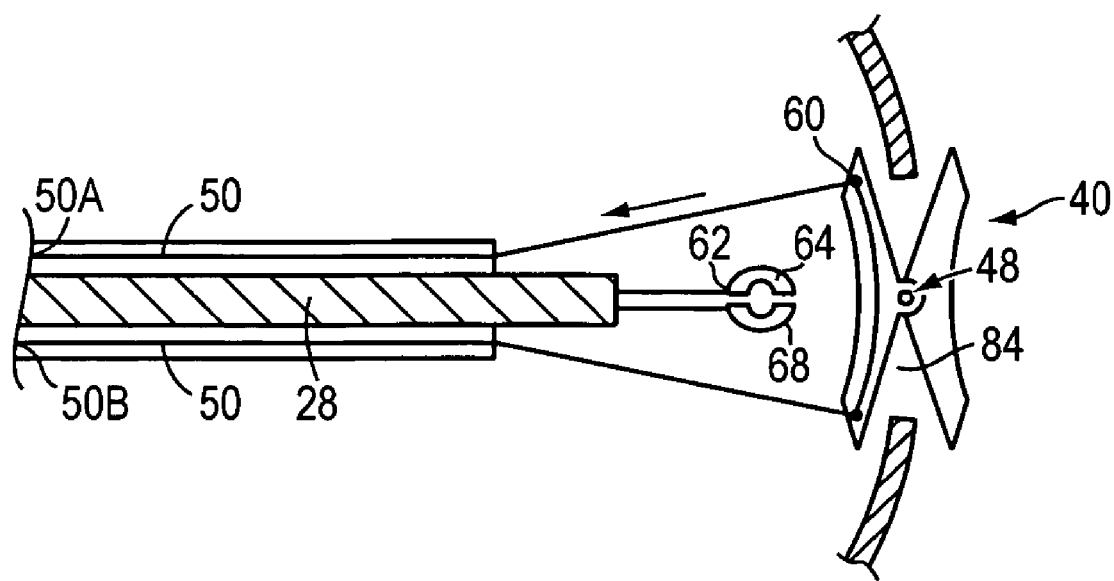

Referring now to FIG. 10C, when the implant 40 is satisfactorily positioned within the cardiac septum patent foramen ovale 84, the operator releases the implant 40. The operator may release the implant 40 by first releasing the jaws 64, 68 of the grasper 62 from the ball 48 and then applying tension to suture end 50A to unravel the quick release knot 60. The suture 50 is pulled away from the implant 40 by releasing suture end 50B and pulling on suture end 50A. Alternatively, the medical operator may release the implant 40 before releasing the grasper 62 by first pulling on suture 50A to unravel the quick release knot 60, pulling the suture 50 away from the implant, and then releasing the jaws 64, 68 of the grasper 62 from the ball 48.

Figure 10D:
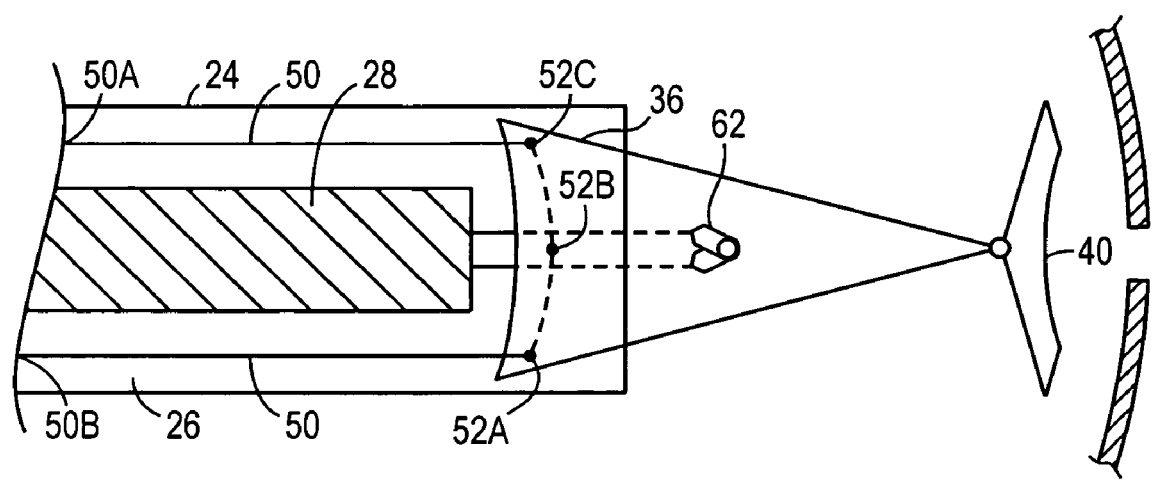

Conversely, as depicted in FIG. 10D, if the operator is not satisfied with the positioning of the implant 40, the operator may apply tension to the suture end 50B, collapsing the proximal portion 36 of the implant 40. The collapsed implant 40 may then be retrieved into the tube 24 of the delivery device 20 by, for example, pulling on the suture end 50B and drawing the collapsed implant 40 back into the tube 24 of the delivery device 20; by advancing the tube 24 over the collapsed implant 40; or by drawing the elongated member 28 while coupled to the collapsed implant 40 back into the tube 24. After the implant 40 has been recovered, the operator may either maneuver the delivery system 20 to reposition the implant 40 or may remove the delivery 20 system from the patient's body.

OTHER EMBODIMENTS

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for delivering a medical implant, comprising:
   a tube comprising a lumen; and
   a suture capable of being releasably joined to the implant, the suture comprising a first end, a second end, and a releasable knot, wherein applying tension to the first end of the suture collapses at least a portion of the implant for introduction into the tubular lumen and applying tension to the second end of the suture releases the suture from the implant.

2. The medical delivery device of claim 1, wherein the suture is capable of being attached to a proximal portion of the implant.

3. The medical delivery device of claim 2, wherein the suture is attached to a coil.

4. The medical delivery device of claim 1, wherein the implant comprises a septal occluder.

5. The medical delivery device of claim 1, wherein the releasable knot comprises a slip knot.

6. The medical delivery device of claim 1, wherein the releasable knot comprises a highwayman's hitch knot.

7. The medical delivery device of claim 1, wherein the first end and the second end of the suture are operatively joined to an actuator.

8. The medical delivery device of claim 1, wherein the suture is capable of being joined to the implant at a plurality of attachment sites.

9. The medical delivery device of claim 1 further comprising a grasper.

10. The medical delivery device of claim 9, wherein the grasper comprises a fixed position jaw.

11. The medical delivery device of claim 9, wherein the grasper comprises a pivotal jaw.

12. The medical delivery device of claim 11 further comprising an elongated member wherein the grasper is joined to the elongated member.

13. The medical delivery device of claim 12, wherein said elongated member is operatively joined to an actuator.

14. A medical delivery system for delivering an implant comprising
a tube comprising a lumen for slideably receiving the implant; and
a suture comprising a first end, a second end, and a knot, wherein the suture is capable of being releasably joined to the implant by the knot, the implant being secured to the suture when tension is applied to the first end of the suture and the implant being released from the suture when tension is applied to the second end of the suture.

15. The medical delivery system of claim 14, wherein said tube is operatively joined to an actuator.

16. The medical delivery system of claim 14, wherein the knot is a slip knot.

17. The medical delivery system of claim 16, wherein tension applied to the first end of the suture tightens the knot and tension applied to the second end of the suture releases the knot.

18. The medical delivery system of claim 17, wherein tension applied to the first end of the suture is capable of collapsing collapses at least a portion of the implant for introduction into the lumen of the tube.

19. The medical delivery system of claim 14, wherein the implant comprises a septal occluder.

20. The medical delivery system of claim 14, further comprising a plurality of sutures.

21. The medical delivery system of claim 20, wherein the tube further comprises at least one separate lumen for slideably receiving at least one of the plurality of sutures.

22. An attachment system for a medical implant, comprising:
a suture comprising a first end, a second end, and a knot, wherein the suture is capable of being releasably joined to the implant by the knot, the implant being secured to the suture when tension is applied to the first end of the suture and the implant being released from the suture when tension is applied to the second end of the suture.

23. A method of occluding a site in a body of a patient, the method comprising:
providing a medical delivery system for a medical implant, comprising:
a tube comprising a lumen;
an implant; and
a suture releasably joined to the implant, the suture comprising a first end, a second end, and a releasable knot, wherein applying tension to the first end of the suture collapses at least a portion of the implant for introduction into the tube lumen and applying tension to the second end of the suture releases the knot; and delivering the implant to an anatomical site in the body of the patient.

24. The method of claim 23, wherein the site is a vessel.

25. The method claim of claim 24, wherein the site is a patent foramen ovale.

* * * * *